United States Patent
Procyshyn et al.

(10) Patent No.: US 10,850,873 B2
(45) Date of Patent: Dec. 1, 2020

(54) APPARATUS AND METHOD FOR ASEPTICALY FILLING PHARMACEUTICAL CONTAINERS WITH A PHARMACEUTICAL FLUID USING ROTARY STAGE

(71) Applicant: Vanrx Pharmasystems Inc., Burnaby (CA)

(72) Inventors: Christopher Procyshyn, Surrey (CA); Juvenal Naing, Belcarra (CA); John Senger, New Westminster (CA); Marcin Cichy, Surrey (CA)

(73) Assignee: VANRX PHARMASYSTEMS INC., Burnaby (CA)

( * ) Notice: Subject to any disclaimer, the term of this patent is extended or adjusted under 35 U.S.C. 154(b) by 573 days.

(21) Appl. No.: 15/453,615

(22) Filed: Mar. 8, 2017

(65) Prior Publication Data
US 2018/0037343 A1 Feb. 8, 2018

Related U.S. Application Data

(60) Provisional application No. 62/371,196, filed on Aug. 4, 2016.

(51) Int. Cl.
*B65B 3/00* (2006.01)
*B65B 55/02* (2006.01)
(Continued)

(52) U.S. Cl.
CPC .......... *B65B 3/003* (2013.01); *A61M 5/1782* (2013.01); *B65B 55/022* (2013.01);
(Continued)

(58) Field of Classification Search
CPC ... A61J 1/10; A61J 1/20; A61J 1/2096; B65B 3/003; B65B 7/161; B65B 55/027; B65D 51/002
See application file for complete search history.

(56) References Cited

U.S. PATENT DOCUMENTS

| 5,799,464 A | 9/1998 | Olsson |
| 5,979,515 A | 11/1999 | Olsson |

(Continued)

FOREIGN PATENT DOCUMENTS

| CA | 2921554 A1 | 2/2015 |
| WO | 2015023924 A2 | 2/2015 |

(Continued)

OTHER PUBLICATIONS

International Preliminary Report on Patentability (PCT/IB2017/001183), dated Feb. 5, 2019.

(Continued)

*Primary Examiner* — Andrew M Tecco
*Assistant Examiner* — Eyamindae C Jallow
(74) *Attorney, Agent, or Firm* — Kevin R. Endman; Brannon Sowers & Cracraft PC (57) ABSTRACT

Systems and methods for aseptically filling pharmaceutical containers with pharmaceutical fluid are disclosed. In one general aspect, these are based on an aseptically sealable chamber that includes a transfer wall to which pre-sealed pharmaceutical source and receiving containers are mounted aseptically. A robotic arm and a syringe store are disposed within the chamber along with a sterilizing facility for establishing in the chamber an aseptic condition. The robotic arm can grip and operate syringes to inject and/or extract pharmaceutical products from the containers by piercing their closures with the needles of the syringes.

31 Claims, 5 Drawing Sheets

(51) Int. Cl.
*A61M 5/178* (2006.01)
*B67C 3/00* (2006.01)
*B65D 41/20* (2006.01)

(52) U.S. Cl.
CPC ............ *B65B 55/027* (2013.01); *B67C 3/004* (2013.01); *B65D 41/20* (2013.01)

(56) References Cited

U.S. PATENT DOCUMENTS

| | | | |
|---|---|---|---|
| 8,196,614 B2* | 6/2012 | Kriheli | A61J 1/2096 141/5 |
| 2002/0029022 A1* | 3/2002 | Naritomi | B29C 45/1676 604/256 |
| 2004/0104243 A1* | 6/2004 | Osborne | B65B 3/003 222/63 |
| 2005/0004706 A1* | 1/2005 | Osborne | B65B 7/161 700/240 |
| 2005/0194059 A1* | 9/2005 | Py | B65B 3/003 141/18 |
| 2006/0231519 A1 | 10/2006 | Py et al. | |
| 2007/0079894 A1* | 4/2007 | Kraus | A61J 1/10 141/319 |
| 2010/0043915 A1* | 2/2010 | Sangi | A61L 2/208 141/11 |
| 2010/0236193 A1 | 9/2010 | Py et al. | |
| 2013/0180618 A1 | 7/2013 | Py et al. | |
| 2014/0128832 A1* | 5/2014 | Larson | A61J 1/18 604/404 |
| 2014/0150379 A1* | 6/2014 | Aguerre | A61J 3/002 53/473 |
| 2015/0335531 A1* | 11/2015 | Yuyama | A61J 1/20 141/18 |
| 2015/0335532 A1* | 11/2015 | Lizari Illarramendi | A61J 3/002 141/1 |
| 2016/0206821 A1* | 7/2016 | Horiuchi | A61M 5/162 |
| 2017/0008651 A1* | 1/2017 | Lizari Illarramendi | B65B 3/04 |

FOREIGN PATENT DOCUMENTS

| | | |
|---|---|---|
| WO | WO-2015023924 A2 * | 2/2015 |
| WO | WO-2015029018 A1 * | 3/2015 |

OTHER PUBLICATIONS

PCT International Search Report (PCT/IB2017/000576), dated Aug. 30, 2017.

* cited by examiner

APPARATUS AND METHOD FOR ASEPTICALY FILLING PHARMACEUTICAL CONTAINERS WITH A PHARMACEUTICAL FLUID USING ROTARY STAGE

BACKGROUND OF THE INVENTION

This application claims priority to U.S. Provisional Application No. 62/371,196, filed Aug. 4, 2017, which is herein incorporated by reference.

FIELD OF THE INVENTION

This present invention relates to the medical field and more particularly to apparatus and associated methods for sterilization of and sterile handling of pharmaceutical materials and containers for pharmaceuticals, including bringing pharmaceuticals into form for administration to medical or veterinary patients. In one aspect, it relates to the programmed and automatic operation of such apparatus.

BACKGROUND

The subject of filling pharmaceuticals into pharmaceutical containers is a major aspect of the Pharmaceuticals Industry. The subject is heavily controlled by various governmental and official bodies in various countries. Technologically, the subject is a challenge in that the pharmaceutical products need to be filled into the containers under very strict aseptic conditions. Very specific procedures are specified for this task to a degree that makes the handling of pharmaceuticals profoundly different from the handling of any other industrial product, including specifically semiconductors, which also demand extreme and consistent environmental conditions. Indeed, the parallels between the handling of semiconductors in semiconductor "clean laboratories" and the handling of pharmaceuticals in aseptic isolators are superficial. They share the use of such "clean laboratories", but there is no inherent aseptic requirement associated with semiconductor manufacture.

The filling of pharmaceutical containers with fluid pharmaceuticals specifically requires the aseptic handling of both the containers and the fluid pharmaceutical itself. This leads to complex mechanisms and procedures, many of which may be automated to one degree or another. Often, the production equipment for fluid pharmaceutical handling is bulky and expensive. This creates a problem for smaller operations, particularly in the small scale production and development environments. As the field has developed, the need for smaller, more compact equipment, particularly in the filling and dispensing of fluid pharmaceuticals has become evident.

The present invention addresses the need for compact small scale filling and dispensing of fluid pharmaceuticals.

SUMMARY OF THE INVENTION

In one general aspect, the invention features a system for aseptically filling pharmaceutical containers with pharmaceutical fluid that includes an aseptically sealable chamber. The aseptically sealable chamber includes a transfer wall with openings that each provide a sealing surface that is aseptically sealable to a container. A robotic arm is disposed within the sealable chamber and has a range of motion that allows it to move a fluid transfer conduit to each of the openings. The system also includes a fluid transfer actuator to drive fluid through the fluid transfer conduit, a sterilizing facility for establishing an aseptic condition within the sealable chamber, and a controller. The controller includes three-dimensional arm control logic to move the fluid transfer conduit to a selected container that sealably passes through one of the openings. It also includes fluid transfer actuation logic to operate the fluid transfer actuator to transfer fluid between a fluid transfer vessel and the selected container.

In preferred embodiments, the fluid transfer conduit can be a syringe needle mounted on a syringe that includes a body and a plunger, with the fluid transfer actuator being a linear actuator that moves the plunger relative to the body. The system can further include at least one container with a pierceable closure sealably passing through one of the openings with the pierceable closure positioned inside the sealable chamber and with the three-dimensional arm control logic being operative to cause the syringe needle to pierce the pierceable closure. The three-dimensional arm control logic and the fluid transfer actuation logic can be operative to transfer fluids from one container to another. The system can further include a syringe store disposed in the interior of the sealable chamber, with the three-dimensional arm control logic being operative to transfer syringes to and from the syringe store. The robotic arm can be an articulated robotic arm. The sealable chamber can be capable of being operated under a positive pressure when sealed.

In another general aspect, the invention features a method for filling pharmaceutical containers with a fluid pharmaceutical product. This method includes providing an aseptically sealable chamber comprising a robotic arm and a transfer wall capable of having aseptically mounted thereto a plurality of pharmaceutical containers pre-sealed with pierceable closures. The aseptically sealable chamber is capable of maintaining an aseptic condition within an interior of the sealable chamber when the pharmaceutical containers are mounted to the transfer wall. The method also includes aseptically mounting to the transfer wall a plurality of pharmaceutical containers aseptically pre-sealed with corresponding pierceable pharmaceutical container closures, with the mounting of the plurality of pharmaceutical containers comprising mounting the plurality of pharmaceutical containers in locations and orientations wherein the corresponding pierceable pharmaceutical container closures are penetrable from within the interior of the sealable chamber. The sealable chamber is provided with a first pharmaceutical syringe comprising a first syringe needle, the chamber is aseptically sealed, and an aseptic condition is established within the interior of the sealable chamber and on all portions of the plurality of pharmaceutical containers exposed to the interior of the sealable chamber. A portion of the first fluid pharmaceutical product can then be transferred between the first syringe and at least one of the plurality of pharmaceutical containers through the corresponding pierceable pharmaceutical container closure via the first syringe needle.

In preferred embodiments the transferring can comprise piercing the corresponding pierceable pharmaceutical container closure with the first syringe needle. The transferring can comprise operating the robotic arm. Providing an aseptically sealable chamber comprising a robotic arm can comprise providing an aseptically sealable chamber comprising an articulated robotic arm with the transferring comprising operating the articulated robotic arm. The transferring can include injecting a portion of the first pharmaceutical product into the one of the plurality of pharmaceutical containers, and providing within the sealable chamber the first pharmaceutical syringe containing the first fluid pharmaceutical product can comprise: aseptically mounting to the transfer wall a first source pharmaceutical container aseptically pre-sealed with a corresponding pierceable first pharmaceutical container closure, with the mounting of the first source pharmaceutical container comprising disposing the first source pharmaceutical container in a location and orientation wherein the first pharmaceutical container closure is penetrable from within the interior of the sealable chamber, piercing the closure of the first source pharmaceutical container with the first syringe needle, and extracting a portion of the first fluid pharmaceutical product from the first source pharmaceutical container into the first pharmaceutical syringe. At least one of the aseptically sealing, the establishing an aseptic condition, the transferring, and the extracting a portion of the first fluid pharmaceutical product can be performed automatically. The method can further comprise establishing within the sealable chamber a positive atmospheric pressure. The establishing within the sealable chamber a positive atmospheric pressure can be performed automatically after the aseptically sealing the sealable chamber. The method can further comprise injecting a portion of a second fluid pharmaceutical product from a second syringe into the at least one of the plurality of pharmaceutical containers through the corresponding pierceable pharmaceutical container closure via a second syringe needle. The providing an aseptically sealable chamber can comprise providing an aseptically sealable chamber comprising a syringe store, with the second syringe being prepared by: aseptically mounting to the transfer wall a second source pharmaceutical container aseptically pre-sealed with a corresponding pierceable second pharmaceutical container closure and containing the second fluid pharmaceutical, with the mounting of the second source pharmaceutical container comprising disposing the second source pharmaceutical container in a location and orientation wherein the second pharmaceutical container closure is penetrable from within the interior of the sealable chamber, operating the robotic arm to place the first syringe in the syringe store, operating the robotic arm to obtain from the syringe store the second pharmaceutical syringe comprising the second syringe needle, operating the robotic arm to pierce the closure of the second source pharmaceutical container with the second syringe needle, and operating the robotic arm to extract a portion of the second fluid pharmaceutical product from the second source pharmaceutical container into the syringe. The establishing an aseptic condition can comprise treating the interior of the sealable chamber and all portions of the at least one pharmaceutical container exposed to the interior of the sealable chamber with at least one of heated water vapor, gaseous hydrogen peroxide, ozone, nitrogen dioxide, ethylene oxide, and glutaraldehyde vapor.

In a further general aspect, the invention features a system for aseptically filling pharmaceutical containers with pharmaceutical fluid that includes means for receiving a plurality of containers while exposing accessible parts of the containers, means for transferring pharmaceutical fluid to and from the containers through the accessible parts of the containers, and means for reaching the accessible parts of the received containers with the means for transferring. The system also includes means for controlling the means for reaching and the means for transferring, means for together isolating the exposed parts of the containers, the means for reaching, and the means for transferring, and means for sterilizing the exposed parts of the containers, the means for reaching, and the means for transferring.

Systems according to the invention can provide a compact and cost-effective way to automatically perform a wide variety of pharmaceutical filling operations in an aseptic environment using readily available pre-sterilized containers with pierceable closures.

BRIEF DESCRIPTION OF THE DRAWINGS

The above mentioned and other features and objects of this invention, and the manner of attaining them, will become more apparent and the invention itself will be better understood by reference to the following description of an embodiment of the invention taken in conjunction with the accompanying drawings, wherein.

Corresponding reference characters indicate corresponding parts throughout the several views. Although the drawings represent embodiments of the present invention, the drawings are not necessarily to scale and certain features may be exaggerated in order to better illustrate and explain the present invention. The flow charts are also representative in nature, and actual embodiments of the invention may include further features or steps not shown in the drawings. The exemplifications set out herein illustrate embodiments of the invention, in one or more forms, and such exemplifications are not to be construed as limiting the scope of the invention in any manner.

DESCRIPTION OF EMBODIMENTS OF THE PRESENT INVENTION

The embodiments disclosed below are not intended to be exhaustive or limit the invention to the precise form disclosed in the following detailed description. Rather, the embodiments are chosen and described so that others skilled in the art may utilize their teachings.

Figure 1:
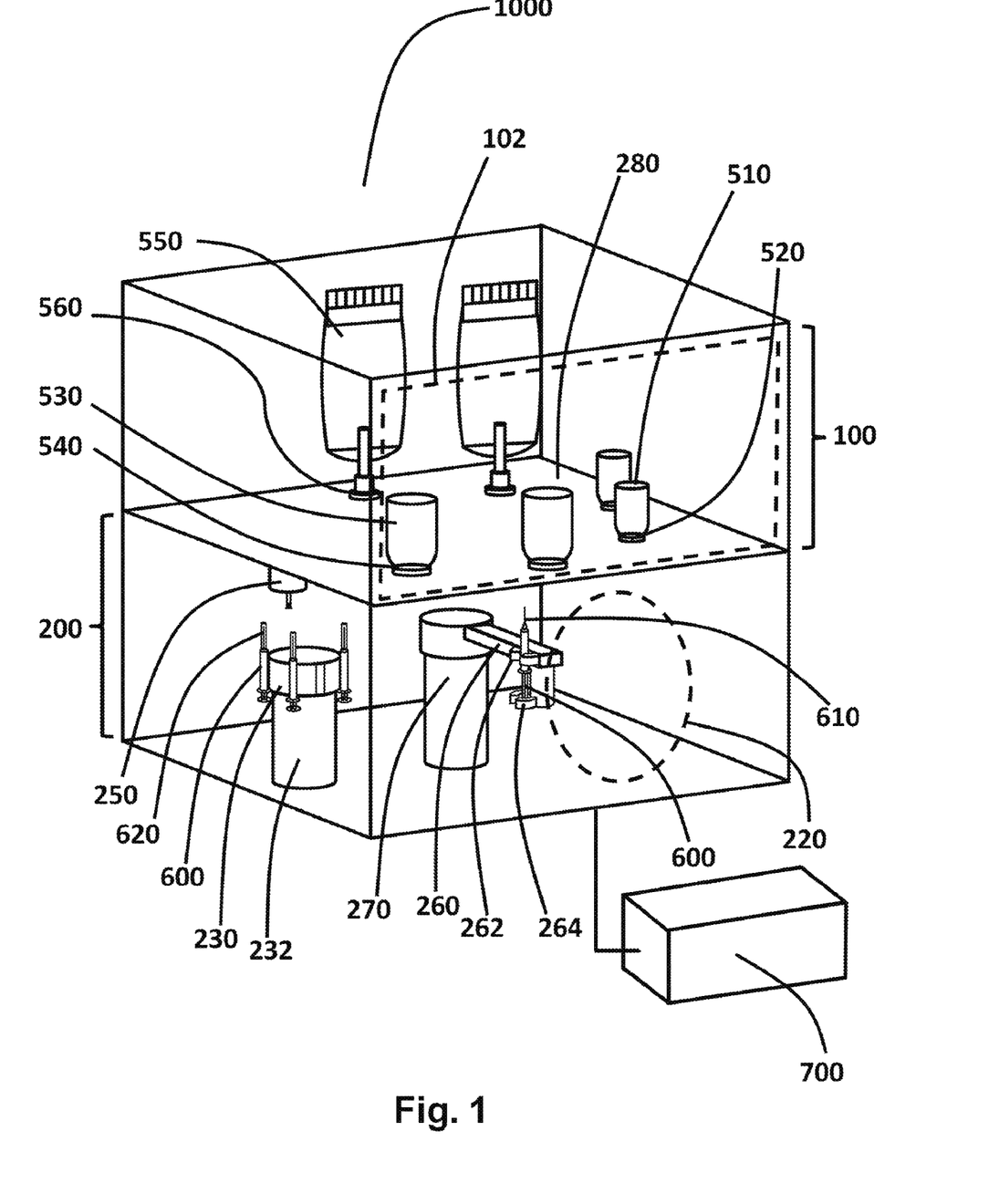
FIG. 1 is a drawing of a first embodiment of an apparatus for filling pharmaceutical containers with a pharmaceutical fluid product.

The present invention relates to an apparatus and method for filing pharmaceutical containers with a pharmaceutical. In FIG. 1, a filling system 1000 comprises a container chamber 100 in communication with an ambient environment and a sealable chamber 200 adjoining the container chamber 100, the sealable chamber 200 being capable of having an aseptic environment established within its interior and capable of maintaining that aseptic environment within its interior. The communication of chamber 100 with the ambient environment may be via a suitable access door 102, schematically shown in broken outline in FIG. 1. The ambient environment may be, for example, a clean room adapted for the handling of pharmaceuticals during production.

Chamber 200 shares with chamber 100 a transfer wall 280 and comprises an aseptically sealable port 220. A variety of suitable port arrangements is contemplated. In some embodiments, port 220 is a simple door with an aseptic seal arrangement to ensure that chamber 200 maintains an aseptic condition. In other embodiments, port 220 may be a more complex door arrangement to ensure the aseptic condition in the interior of chamber 200. In some embodiments, chamber 100 is completely open. This is the equivalent of there being no distinct first chamber 100.

The interior of sealable chamber 200 may be rendered aseptic by any one or more of a number of treatments, including specifically treatments with sterilants, such as steam, hydrogen peroxide vapor, ozone, nitrogen dioxide, and ethylene oxide. The structures and mechanisms to perform such sterilization steps are well known in the art and, in the interest of clarity, are not shown in FIG. 1.

The terms "aseptic" and "sterilize" and their derivatives are to be understood as follows for the purposes of the present specification. Establishing an aseptic condition in the interior of a chamber shall be understood to mean establishing that condition throughout the internal atmosphere of the chamber as well as on substantially all exposed interior surfaces of the chamber. This shall include the surfaces of all items, containers, subsystems and the like exposed to the interior atmosphere of the chamber. The degree of sterilization may in some practical cases not be total. Extremely tight crevices or microcrevices may exist in the interior of the chamber, for example, such that a sterilizing gas or vapor may not perfectly penetrate into such tight regions. This is acknowledged both in the industry and in the standards set for industry.

As will be described below, some embodiments of the invention involve containers of which portions of their exterior surfaces are exposed to the internal atmosphere of a chamber. When the interior of the chamber is being sterilized, the portion of the surface of the container that is exposed to the internal atmosphere of the chamber is sterilized in the process. The action of establishing an aseptic condition within the interior of the chamber and "sterilizing the interior of the chamber" shall have the same meaning in this specification.

Introducing into the interior of a chamber with an aseptic condition an item of which the surfaces are not suitably sterilized destroys the existing aseptic condition within the chamber. Conversely, introducing an aseptic or sterilized item into an interior of a chamber that does not have an aseptic condition within that interior does not render that interior aseptic. In fact, all it does is to destroy the aseptic condition of the surface of the item so introduced. Similarly, introducing filtered air, even with all biological entities filtered out, into an unsterilized chamber does not in any way sterilize the chamber or render it aseptic to a degree acceptable in the pharmaceutical industry. The reason is that the interior surfaces of the chamber are not sterilized by the introduction of such air. All that is achieved is to contaminate the filtered air with active biological species resident on the interior surfaces of the unsterilized chamber.

In the interest of clarity and completeness, it should also be recorded that in the art the term "aseptic" is also sometimes used in association with the introduction of pharmaceutical fluids along aseptic tubes into bodies within controlled chambers. In such cases the term in the art refers to the condition inside the tube or to the fact that the pharmaceutical fluid may be filtered to a suitable degree. This in no way sterilizes or renders aseptic the interior of the chamber in question. The aseptic condition in such cases is confined to the interior of the tube bearing the pharmaceutical stream. Such streams are often filtered to a high degree, but such filtering affects only the interior of the particular tube and does not in any way sterilize the interior of the chamber.

In some prior art systems, containers introduced into a chamber for the purposes of being filled with a pharmaceutical are routed through sterilizing subsystems. This kills biological species on the containers. When such sterilized containers are introduced into the chamber when the chamber itself is not aseptic the containers lose their aseptic condition as biological species contained within the chamber will deposit on the previously aseptic containers.

Standards for clean rooms exist from both the United States Federal Government and ISO (International Standards Organization). These specify in great detail the allowed particulate content of a cubic volume of air in such a clean room facility. But none of these standards directly address the matter of biological species present on surfaces in the room. This serves to make the point that a chamber cannot be rendered aseptic by the management of its atmosphere or airflow only. Nor, conversely, can the chamber be rendered aseptic by the sterilization of only the surfaces of its interior. Rating a pharmaceutical or semiconductor clean room at any quality level, therefore, including "Class 100", "Class 10" or "Class 1", even when employing laminar flow hoods and the like or any quality of HEPA (High Efficiency Particulate Air) filters or ULPA (Ultra Low Particulate Air) filters, is not sufficient to assure an aseptic chamber at least because these standards do not provide for an assurable means to render the surfaces of the room sterile or aseptic.

The text "Guideline for Disinfection and Sterilization in healthcare Facilities, 2008" by Rutala et al from the Center for Disease Control lists a compendium of mechanisms and methods for sterilization. Our concern in this specification is specifically with those mechanisms for sterilizing the interior of a chamber; that is, sterilizing both the interior surfaces and the atmosphere within the chamber. Given the requirements, vapor base methods are most appropriate to the task. These include, but are not limited to, treatment with heated water vapor, hydrogen peroxide vapor, ozone, nitrogen dioxide, ethylene oxide, glutaraldehyde vapor or other suitable sterilizing gases and vapors. In one suitable method appropriate to the present invention, the sterilization is by means of hydrogen peroxide vapor which is then flushed using ozone before the chamber is employed in the filling of pharmaceutical containers.

Sealable chamber 200 may comprise in its interior a robotic rotary arm 260 mounted on a rotary stage 270. Rotary stage 270 may also be an extensible stage so that robotic arm 260 may be raised and lowered vertically.

Robotic rotary arm 260 may comprise two grips 262 and 264 disposed and configured for gripping a syringe 600 and for moving a plunger of the syringe 600 with respect to the cylinder of the syringe 600. In FIG. 1, grip 264 is disposed and configured to grip the plunger mechanism of syringe 600 and to move it with respect to the cylinder of syringe 600, which is held stationary relative to robotic rotary arm 260 by grip 262. By rotating rotary stage 270, raising or lowering rotary stage 270, and operating grip 264, the syringe 600 may therefore be positioned anywhere on a cylindrical surface determined by a radius of robotic rotary arm 260 and the vertical adjustment range of rotary stage 270, and the syringe 600 may be operated to perform an injection procedure or extraction procedure while so positioned. In other embodiments, robotic rotary arm 260 may be extensible to thereby allow syringe 600 to be positioned in a wider range of positions interior to the cylindrical surface defined by the maximum extendible radius of robotic rotary arm 260. In the embodiment shown in FIG. 1, robotic arm 260 is specifically a non-articulated robotic arm. To the extent that the present invention seeks simplicity and compactness, there is no restriction for robotic arm 260 to specifically emulate the human arm in its articulation. Yet further robotic arm arrangements are contemplated and will be discussed later below.

Sealable chamber 200 may further comprise in its interior a syringe store. In the embodiment shown in FIG. 1, the syringe store is a carousel 230 mounted on a stage 232. Carousel 230 is configured for holding a plurality of syringes 600 having syringe caps 620. In some embodiments, stage 232 may be a vertically extensible stage bearing further carousels 230. In such embodiments, stage 232 may be disposed and configured to raise and lower the carousel 230. Carousel 230 is disposed in a position that allows robotic rotary arm 260 to collect and return syringes 600 from and to carousel 230. To this end, carousel 230 is a rotary carousel allowing different ones of syringes 600 to be accessible to the grippers 262 and 264 of robotic rotary arm 260.

Sealable chamber 200 may further comprise in its interior a syringe capping station 250, disposed and arranged for robotic rotary arm 260 to engage syringes 600 with syringe capping station 250 to thereby remove syringe caps 620 from syringes 600 or to return syringe caps 620 to syringes 600 after the use of syringes 600.

By way of example, rotary stage 270 may rotate arm 260 clockwise (looking down vertically in FIG. 1) in order to collect a syringe 600 from carousel 230, while rotary stage 270 may rotate arm 260 anti-clockwise (looking down vertically in FIG. 1) in order to engage a syringe 600 with capping station 250 in order to remove a cap 620 from the syringe 600 and thereby expose hollow syringe needle 610, for example a hypodermic needle.

Robotic arm 260 may be controlled by controller 700 in communication with robotic arm 260. In FIG. 1 controller 700 is shown as a distinct separate unit, but in other embodiments it may be incorporated into either chamber 100 or chamber 200. Controller 700 may comprise a suitable computer or microcontroller with memory to store a software program and data provided by the operator. The operating of robotic arm 260 may comprise the operating of rotary stage 270 and the operating of grips 262 and 264. In some embodiments, controller 700 may also operate the sterilization facility not shown in FIG. 1. Controller 700 may further control the rotation of carousel 230 and stage 232. Controller 700 may also control the sealing of chamber 200 and the pressure inside of chamber 200. This allows the automation of the processes employed in system 1000.

A variety of containers may be disposed within the interior of chamber 100. In FIG. 1 the examples given are rigid pharmaceutical containers 510 of a first size, rigid pharmaceutical containers 530 of a second size, and intravenous (IV) bags 550, being sealed to the transfer wall 280 by container sealing structures 520, 540 and 560 respectively. Transfer wall 280 may have corresponding holes to allow access by needle 610 to the various containers while an aseptic condition is maintained in the interior of chamber 200.

Figure 2A:
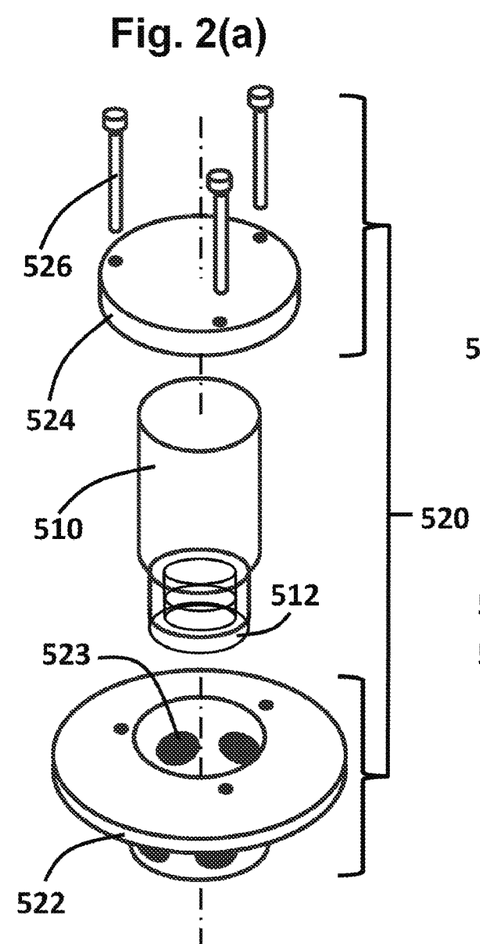
FIG. 2(a) is an exploded view of one example aseptic sealing structure for sealing a pharmaceutical container to a transfer wall between an aseptic interior volume and an ambient volume of an apparatus for aseptically filling pharmaceutical containers with a pharmaceutical fluid.

In FIG. 1 container sealing structures 520, 540 and 560 are merely schematically indicated. FIGS. 2(a), (b) and (c) show an exploded view, assembled view, and cross-section respectively of one example aseptic sealing structure 520 by which container 510, for example, may be aseptically sealed to transfer wall 280 in order to give the needle 610 of syringe 600 access to the interior of the aseptically sealed container 510 without compromising the aseptic condition maintained in the interior of sealable chamber 200. Sealing structure 540 may comprise a differently sized arrangement of the same design to seal container 530 to transfer wall 280. In FIG. 1 two sizes of rigid pharmaceutical containers are shown. In general, fewer or more containers may be employed in chamber 100.

Figure 2B:
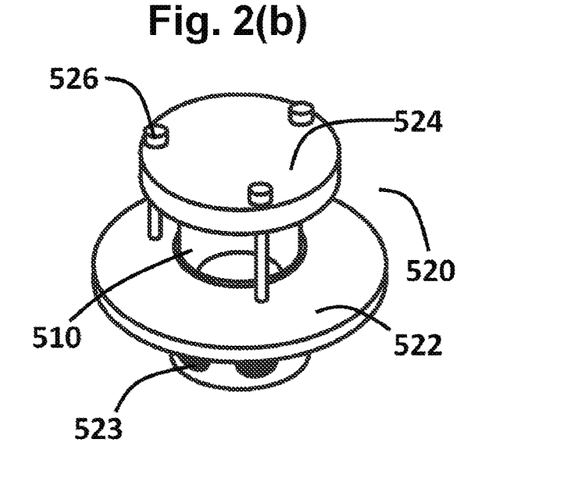
FIG. 2(b) is a view of the example aseptic sealing structure of FIG. 2(a) when assembled.
Figure 2C:
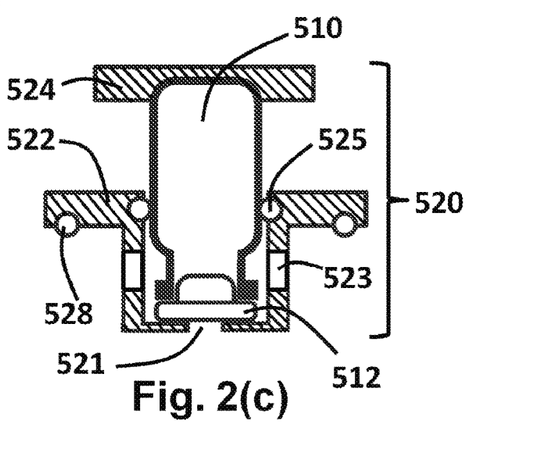
FIG. 2(c) is a cross-sectional view of the assembled aseptic sealing structure of FIG. 2(b)

In one example, shown in FIG. 2(a), sealing structure 520 comprises flange structure 522 having a recessed portion with vapor communication holes 523. Container 510, aseptically sealed with a compressible pierceable closure 512, for example a thermoplastic stopper, is placed upside down into the recessed portion of flange 522 with pierceable closure 512 over hole 521. Cap 524 may then be placed over the upward facing bottom of the container 510 and tightened down onto flange 522 by means of bolts 526. FIG. 2(b) is an isometric view of the completed arrangement of container 510 with closure 512 mounted in sealing structure 520. FIG. 2(c) shows how container 510 is sealed aseptically to sealing structure 520 by means of o-rings 525 and the compressible pierceable closure 512. Sealing structure may be aseptically sealed to transfer wall 280, for example using o-rings 528 and suitable bolts (not shown).

When flange 522 is mounted to transfer wall 280, the recessed portion of flange 522 extends into the interior of chamber 200. Any gas or vapor employed to sterilize the interior of sealable chamber 200 may move through holes 523 in order to sterilize any portion of the exterior surface of container 510 that is accessible to sterilizing vapor or gas employed in the interior of sealable chamber 200. In this specification the phrase "sterilizable portion" is used to describe that portion of the exterior surface of a pharmaceutical container aseptically sealed to the transfer wall 280 that is accessible to sterilizing vapor or gas employed to establish an aseptic condition in the interior of sealable chamber 200.

With flange 522 mounted to transfer wall 280, robotic rotary arm 260 may position and manipulate syringe 600 in order to pierce the pierceable closure 512 through hole 521 with hollow needle 610. With the needle within the interior volume of container 512, a portion of any fluid in syringe 600 may be injected into container 510, or a portion of any fluid in container 512 may be extracted from container 510 into syringe 600 for use elsewhere.

Figure 2D:
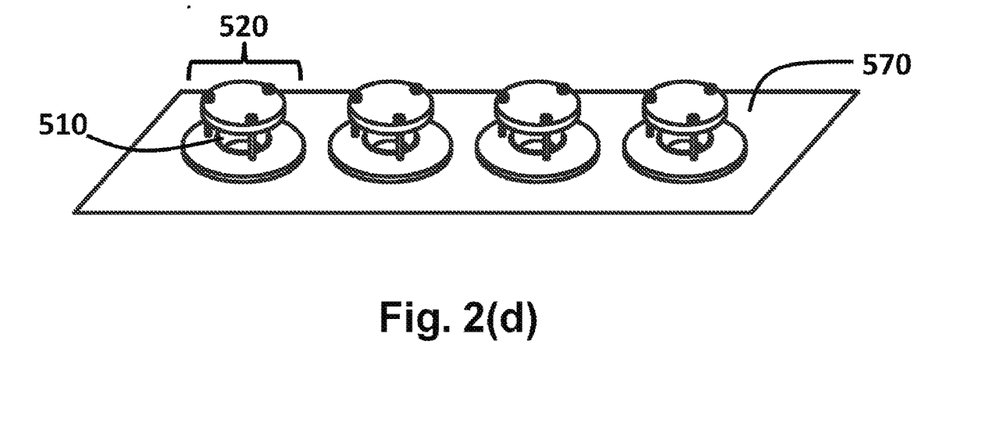
FIG. 2(d) is a drawing of an arrangement for aseptically sealing a plurality of pharmaceutical containers to a sealing plate that may be aseptically sealable to a transfer wall between an aseptic interior volume and an ambient volume of an apparatus for aseptically filling pharmaceutical containers with a pharmaceutical fluid.

FIG. 2(d) shows a container mounting plate 570 to which a plurality of container sealing structures 520 may be aseptically sealed in the same way, described above, as used to seal sealing structure 520 to transfer wall 280. In this particular embodiment, plate 570 is aseptically sealed to transfer wall 280 by means of, for example without limitation, suitable o-rings and bolts (not shown). Transfer wall 280 may have corresponding holes to accommodate the plurality of pierceable closures 512 and flanges 522.

Figures 2E, 2F:
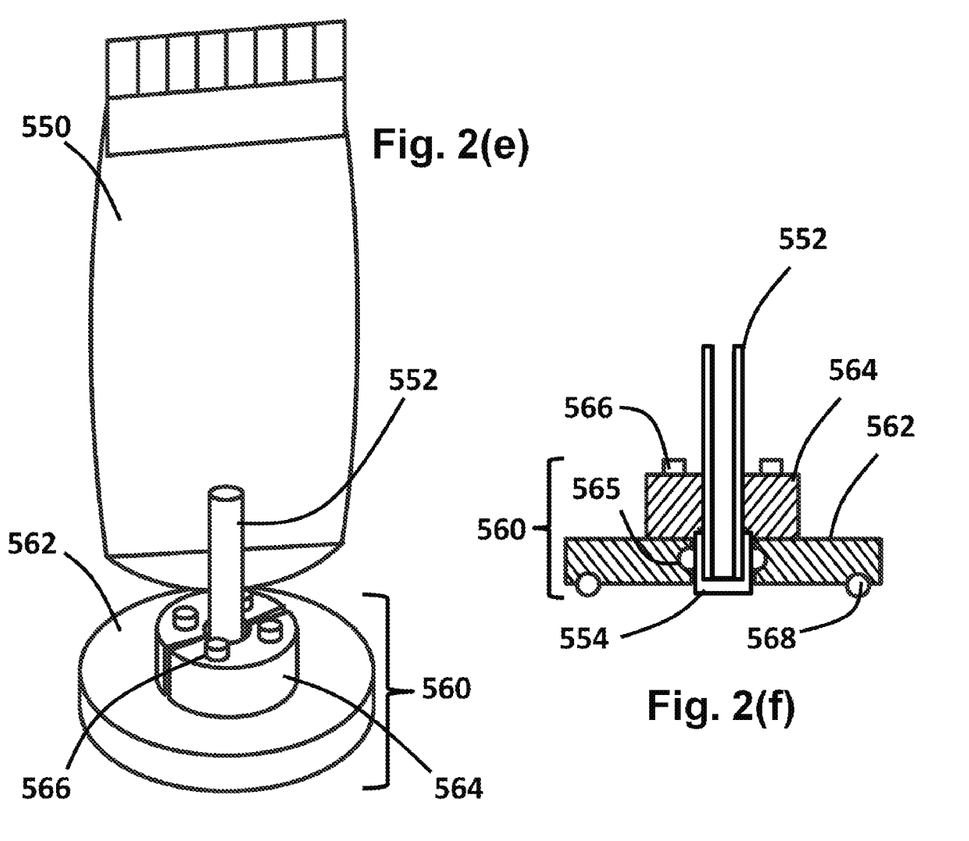
FIG. 2(e) is a drawing of one example aseptic sealing structure for sealing a intra-venous bag pharmaceutical container to a transfer wall between an aseptic interior volume and an ambient volume of an apparatus for aseptically filling pharmaceutical containers with a pharmaceutical fluid.
FIG. 2(f) is a cross-sectional view of the structure of FIG. 2(e)

One particularly useful type of pharmaceutical container is the intra-venous bag (IV-bag). FIG. 2(e) and FIG. 2(f) are isometric and cross-sectional views respectively of an example sealing structure 560 for the aseptic sealing of an IV-bag container 550 to transfer wall 280. IV-bag tube 552 is aseptically sealed with pierceable closure 554. Pierceable closure 554 may be aseptically sealed to flange 562 by means of o-ring 565. Two half-annular caps 564 hold pierceable closure 554 to flange 562 by means of bolts 566. Sealing structure 560 may be aseptically sealed to transfer wall 280 by means of o-ring 568 and bolts (not shown).

Figure 2G:
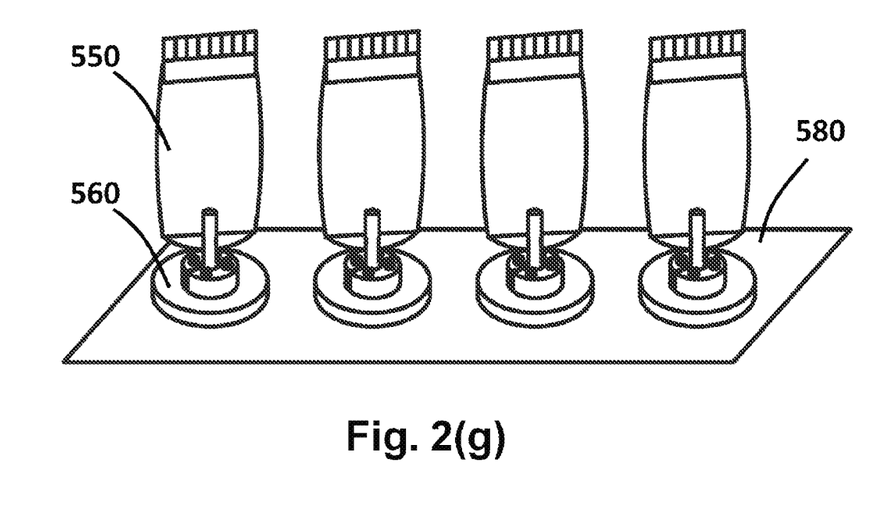
FIG. 2(g) is a drawing of an arrangement for aseptically sealing a plurality of intra-venous bag pharmaceutical containers to a sealing plate that may be aseptically sealable to a transfer wall between an aseptic interior volume and an ambient volume of an apparatus for aseptically filling pharmaceutical containers with a pharmaceutical fluid.

FIG. 2(g) shows a container mounting plate 580 to which a plurality of container sealing structures 560 may be aseptically sealed in the same way, described above, as used to seal sealing structure 560 to transfer wall 280. In this particular embodiment, plate 580 is aseptically sealed to transfer wall 280 by means of, for example without limitation, suitable o-rings and bolts (not shown). Transfer wall 280 may have corresponding holes to accommodate the plurality of pierceable closures 554 and flanges 562.

In embodiments where chamber 200 is absent, the fact that the invention allows for the pharmaceutical containers 510, 530, 550 to be mounted to transfer wall 480 under ambient conditions becomes particularly evident.

To ensure that atmosphere external to chamber 200 cannot leak into chamber 200, chamber 200 is capable of operating under a positive pressure with respect to the environment outside chamber 200. This aids in ensuring the aseptic condition inside chamber 200.

Figure 3:
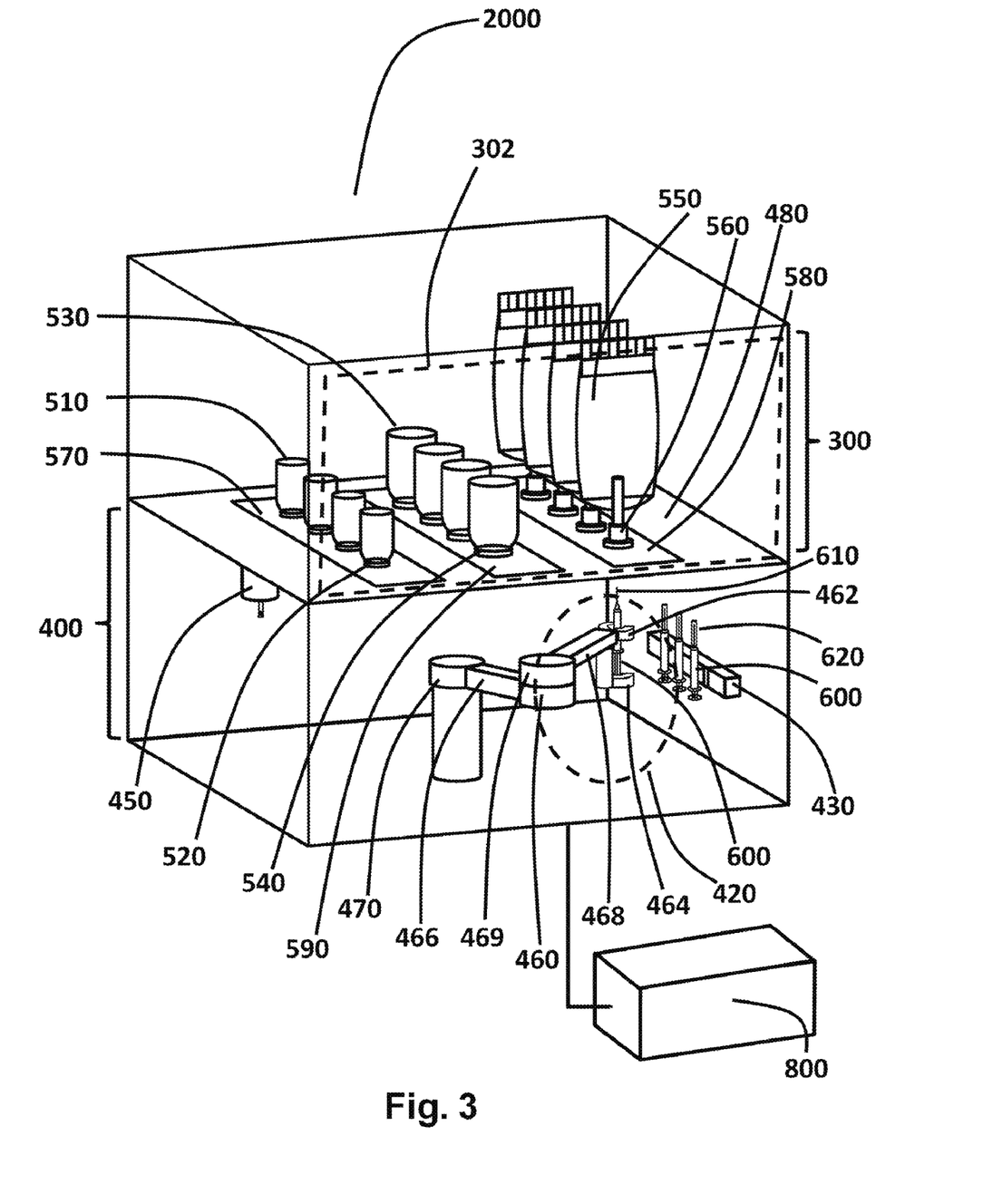
FIG. 3 is a drawing of a second embodiment of an apparatus for filling pharmaceutical containers with a pharmaceutical fluid product.

A further embodiment of the apparatus of the invention is shown in and FIG. 3 in which, a filling system 2000 comprises a first chamber 300 in communication with an ambient environment and a second sealable chamber 400 adjoining the first chamber 300, the second chamber 400 being capable of having an aseptic environment established within its interior and capable of maintaining that aseptic environment within its interior. The communication of chamber 300 with the ambient environment may be via a suitable access door 302, schematically shown in broken outline in FIG. 3. The ambient environment may be, for example, a clean room adapted for the handling of pharmaceuticals during production.

Chamber 400 shares with chamber 300 a transfer wall 480 and comprises an aseptically sealable port 420. A variety of suitable port arrangements is contemplated. In some embodiments, port 420 is a simple door with an aseptic seal arrangement to ensure that chamber 400 maintains an aseptic condition. In other embodiments, port 420 may be a more complex door arrangement to ensure the aseptic condition in the interior of chamber 400. In some embodiments, chamber 300 is completely open. This is the equivalent of there being no distinct first chamber 300. This emphasizes the point that the invention allows for the pharmaceutical containers 510, 530, 550 to be mounted to transfer wall 480 under ambient conditions.

The interior of chamber 400 may be rendered aseptic by any one or more of a number of treatments, including specifically treatment with steam, hydrogen peroxide vapor, ozone, nitrogen dioxide, and ethylene oxide. The structures and mechanisms to perform such sterilization steps are well known in the art and, in the interest of clarity, are not shown in FIG. 3.

Chamber 400 may comprise in its interior a robotic arm 460 mounted on a rotary stage 470. Rotary stage 470 may also be an extensible stage so that robotic arm 460 may be raised and lowered vertically. Robotic arm 460 may be an articulated robotic arm comprising first 466 and second 468 arms that articulate with respect to each other about a common rotary elbow 469. Robotic arm 460 may comprise two grips 462 and 464 disposed and configured for gripping a syringe 600 and for moving a plunger of the syringe 600 with respect to the cylinder of the syringe 600. In FIG. 3, grip 464 is disposed and configured to grip the plunger mechanism of syringe 600 and to move it with respect to the cylinder of syringe 600, which is held stationary relative to arm 468 by grip 462. By rotating rotary stage 470, raising or lowering rotary stage 470, articulating robotic arm 460, and operating grip 264, the syringe 600 may therefore be positioned over a wide range of positions in the interior of chamber 400, and the syringe 600 may be operated to perform an injection procedure or extraction procedure while so positioned.

Chamber 400 may further comprise in its interior a syringe store 430 for holding a plurality of syringes 600 having syringe caps 620. Syringe store 430 is disposed in a position that allows robotic arm 460 to collect and return syringes 600 from and to syringe store 430.

Chamber 400 may further comprise in its interior a syringe capping station 450, disposed and arranged for robotic rotary arm 460 to engage syringes 600 with syringe capping station 450 to thereby remove caps 620 from syringes 600 to thereby expose hollow syringe needle 610, for example a hypodermic needle, or to return caps 620 to syringes 600 after the use of syringes 600.

Robotic arm 460 may be controlled by controller 800 in communication with robotic arm 460. In FIG. 3 controller 800 is shown as a distinct separate unit, but in other embodiments it may be incorporated into either chamber 300 or chamber 400. Controller 800 may comprise a suitable computer or microcontroller with a memory to store a software program and data provided by the operator. The operating of robotic arm 460 may comprise the operating of rotary stage 470 and the operating of grips 462 and 464. In some embodiments, controller 800 may also operate the sterilization facility not shown in FIG. 3. Controller 800 may also control the sealing of chamber 400 and the pressure inside of chamber 400. This allows the automation of the processes employed in system 2000.

A variety of containers may be disposed within the interior of chamber 300. In FIG. 3 the examples given are rigid pharmaceutical containers 510 of a first size, rigid pharmaceutical containers 530 of a second size, and intravenous (IV) bags 550. As shown in FIG. 3, a plurality of containers 510 may be aseptically sealed to container mounting plate 570 as already described, and container mounting plate 570 may then be aseptically sealed to transfer wall 480. As shown in FIG. 3, the same arrangement may be made with respect to differently sized rigid containers 530 and container mounting plate 590. A plurality of IV-bags 550 may be aseptically sealed to container mounting plate 580 as already described, and container mounting plate 580 may then be aseptically sealed to transfer wall 480. In an alternative embodiment, these containers 510, 530 and 550 may be aseptically sealed directly to transfer wall 480 in exactly the same way (not shown in FIG. 3) as they are described above to be sealed to transfer wall 280. The use of an articulated arm 460 allows the linearly arranged containers to be easily accessed by syringe 600. Transfer wall 480 may have corresponding holes to allow access by needle 610 to the various containers while an aseptic condition is maintained in the interior of chamber 400.

Robotic rotary arm 460 may position and manipulate syringe 600 in order to pierce the pierceable closure 512 through hole 521 with hollow needle 610. With the needle within the interior volume of container 512, a portion of any fluid in syringe 600 may be injected into container 510, or a portion of any fluid in container 512 may be extracted from container 510 into syringe 600 for use elsewhere.

To ensure that atmosphere external to chamber 400 cannot leak into chamber 400, chamber 400 is capable of operating under a positive pressure with respect to the environment outside chamber 400. This aids in ensuring the aseptic condition inside chamber 400. The filter and pump systems required to establish such positive pressure are well understood by those skilled in the art and will not be dwelt upon in this specification.

Figure 4:
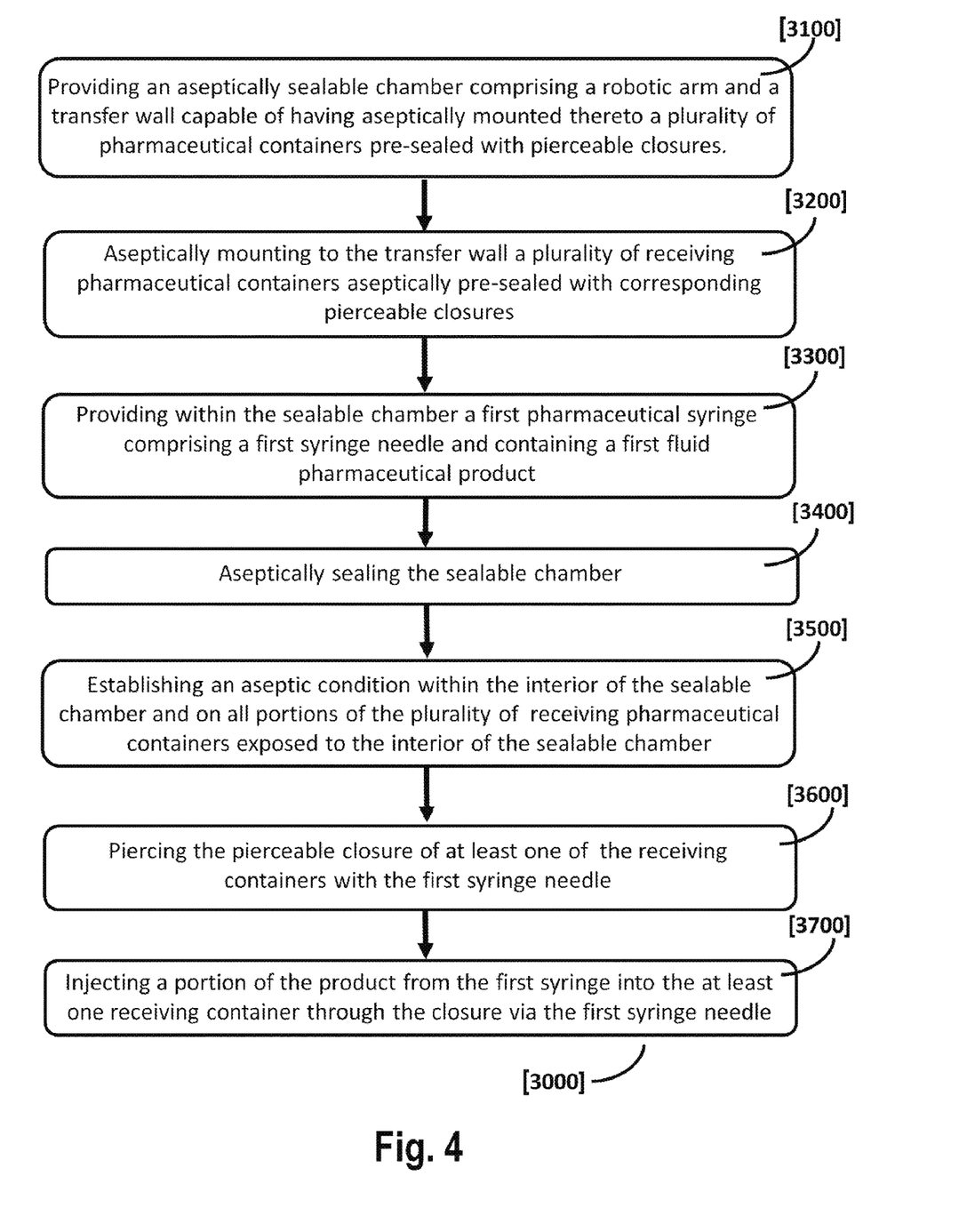
FIG. 4 is a flow diagram of a method for filling a pharmaceutical container with a fluid pharmaceutical product.

In a further aspect described at the hand of the flow chart of FIG. 4, a method [3000] is provided for filling pharmaceutical containers with a fluid pharmaceutical product. The method [3000] comprises: providing [3100] an aseptically sealable chamber 200,400 comprising a robotic arm 260,460 and a transfer wall 280,480 capable of having aseptically mounted thereto a plurality of pharmaceutical containers 510,530,550 pre-sealed with pierceable closures 512,554; aseptically mounting [3200] to the transfer wall 280,480 a plurality of receiving pharmaceutical containers 510,530, 550 aseptically pre-sealed with corresponding pierceable closures 512,554; providing [3300] within the sealable chamber 200,400 a first pharmaceutical syringe 600 comprising a first syringe needle 610 and containing a first fluid pharmaceutical product; aseptically sealing [3400] the sealable chamber 200,400; establishing [3500] an aseptic condition within the interior of the sealable chamber 200,400 and on all portions of the plurality of receiving pharmaceutical containers 510,530,550 exposed to the interior of the sealable chamber 200,400; piercing [3600] the pierceable closure 512,554 of at least one of the receiving containers 510,530,550 with the first syringe needle 610; and injecting [3700] a portion of the product from the first syringe 600 into the at least one receiving container 510,530,550 through the closure 512,554 via the first syringe needle 610. The providing [3100] an aseptically sealable chamber 200,400 may comprise providing an aseptically sealable chamber 200,400 comprising an articulated robotic arm 260,460 and the injecting [3700] may comprise operating the articulated robotic arm 260,460.

The providing [3300] a first syringe 600 within the sealable chamber 200,400 may comprise: aseptically mounting to the transfer wall 280,480 a first source pharmaceutical container containing the first fluid pharmaceutical product and aseptically pre-sealed with a corresponding pierceable closure wherein the mounting of the first source container comprises disposing the first source container in a location and orientation wherein its associated closure is penetrable from within the interior of the sealable chamber 200,400; piercing the associated closure with the first syringe needle 610; and extracting a portion of the first fluid pharmaceutical product from the first source pharmaceutical container into the first pharmaceutical syringe 600.

At least one of the aseptically sealing [3400], the establishing an aseptic condition [3500], the piercing [3600], the injecting [3700], and the extracting a portion of the first fluid pharmaceutical product is performed automatically. The method may further comprise establishing within the sealable chamber 200,400 a positive atmospheric pressure and establishing the pressure may be performed automatically after the aseptically sealing [3400] the sealable chamber 200,400.

The method may further comprise: second injecting a portion of a second fluid pharmaceutical product from a second syringe into the at least one of the plurality of receiving pharmaceutical containers through the corresponding pierceable closure via an associated second syringe needle. The providing [3100] an aseptically sealable chamber 200,400 may comprise providing an aseptically sealable chamber 200,400 comprising a syringe store 230, 430 and the second injecting may comprise: aseptically mounting to the transfer wall a second source pharmaceutical container aseptically pre-sealed with a corresponding pierceable closure and containing the second fluid pharmaceutical wherein the mounting of the second source pharmaceutical container comprises disposing the second source pharmaceutical container in a location and orientation wherein the second source pharmaceutical container closure is penetrable from within the interior of the sealable chamber 200,400; operating the robotic arm 260,460 to place the first syringe in the syringe store 230,430; operating the robotic arm 260,460 to obtain from the syringe store 230, 430 the second pharmaceutical syringe comprising the second syringe needle; operating the robotic arm 260,460 to pierce the closure of the second source pharmaceutical container with the second syringe needle; and operating the robotic arm 260,460 to extract a portion of the second fluid pharmaceutical product from the second source pharmaceutical container into the syringe.

The establishing an aseptic condition may comprise treating the interior of the sealable chamber 200,400 and all portions of the at least one receiving pharmaceutical container exposed to the interior of the sealable chamber 200,400 with at least one of heated water vapor, gaseous hydrogen peroxide, ozone, nitrogen dioxide, ethylene oxide and glutaraldehyde vapor.

Systems according to the invention can allow a variety of dispensing operations, including but not limited to pharmaceutical compounding operations. Different amounts of an active ingredient can be extracted from a source container and added to receiving containers that are prefilled with an inactive ingredient, for example, allowing the different receiving containers to hold different doses of an active ingredient. Different active and/or inactive ingredients can also be extracted from two or more different source containers and added to one or more receiving containers, allowing more complex formulations. Depending on the selected sequencing for a particular dispensing operation, the system may need to switch syringes to avoid cross contamination.

The system described above has been implemented in connection with special-purpose software running on a general-purpose computer platform, but the underlying logic could also be embodied in whole or in part using special-purpose hardware. And while the system can be broken into the series of modules and steps shown for illustration purposes, one of ordinary skill in the art would recognize that it is also possible to combine them and/or split them differently to achieve a different breakdown, and that the functions of such modules and steps can be arbitrarily distributed and intermingled within different entities, such as routines, files, and/or machines. Moreover, different providers can develop and operate different parts of the system.

Embodiments of the present invention addresses the need for compact small scale filling and dispensing of fluid pharmaceuticals and confines only essential aseptic subsystems to an aseptic chamber, whilst making it possible to handle aseptically sealed pharmaceutical containers in the ambient environment outside the aseptic chamber.

While this invention has been described as having an exemplary design, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A method for filling pharmaceutical containers with a fluid pharmaceutical product, the method comprising:
   providing an aseptically sealable chamber comprising a robotic arm and a transfer wall capable of having aseptically mounted thereto a plurality of pharmaceutical containers pre-sealed with pierceable closures, wherein the aseptically sealable chamber is capable of maintaining an aseptic condition within an interior of the sealable chamber when the pharmaceutical containers are mounted to the transfer wall,
   aseptically mounting to the transfer wall a plurality of pharmaceutical containers aseptically pre-sealed with corresponding pierceable pharmaceutical container closures, wherein the mounting of the plurality of pharmaceutical containers comprises mounting the plurality of pharmaceutical containers in locations and orientations wherein the corresponding pierceable pharmaceutical container closures are penetrable from within the interior of the sealable chamber, and the step of aseptically mounting to the transfer wall a plurality of pharmaceutical containers includes using at least one sealing structure to mount at least one container to the transfer wall, the sealing structure includes a flange having a recessed portion, and the recessed portion includes a vapor communication hole,
   providing within the sealable chamber a first pharmaceutical syringe comprising a first syringe needle,
   aseptically sealing the sealable chamber,
   establishing an aseptic condition within the interior of the sealable chamber and on all portions of the plurality of pharmaceutical containers exposed to the interior of the sealable chamber, and
   transferring a portion of the first fluid pharmaceutical product between the first syringe and at least one of the plurality of pharmaceutical containers through the corresponding pierceable pharmaceutical container closure via the first syringe needle.

2. The method of claim 1, wherein the transferring comprises piercing the corresponding pierceable pharmaceutical container closure with the first syringe needle.

3. The method of claim 1, wherein the transferring comprises operating the robotic arm.

4. The method of claim 1, wherein providing an aseptically sealable chamber comprising a robotic arm comprises providing an aseptically sealable chamber comprising an articulated robotic arm and the transferring comprises operating the articulated robotic arm.

5. The method of claim 1, wherein the transferring includes injecting a portion of the first pharmaceutical product into the one of the plurality of pharmaceutical containers, and wherein providing within the sealable chamber the first pharmaceutical syringe containing the first fluid pharmaceutical product comprises:
   aseptically mounting to the transfer wall a first source pharmaceutical container aseptically pre-sealed with a corresponding pierceable first pharmaceutical container closure, wherein the mounting of the first source pharmaceutical container comprises disposing the first source pharmaceutical container in a location and orientation wherein the first pharmaceutical container closure is penetrable from within the interior of the sealable chamber,
   piercing the closure of the first source pharmaceutical container with the first syringe needle, and
   extracting a portion of the first fluid pharmaceutical product from the first source pharmaceutical container into the first pharmaceutical syringe.

6. The method of claim 5, wherein at least one of the aseptically sealing, the establishing an aseptic condition, the transferring, and the extracting a portion of the first fluid pharmaceutical product is performed automatically.

7. The method of claim 5, further comprising establishing within the sealable chamber a positive atmospheric pressure.

8. The method of claim 7, wherein the establishing within the sealable chamber a positive atmospheric pressure is performed automatically after the aseptically sealing the sealable chamber.

9. The method of claim 5, further comprising
   injecting a portion of a second fluid pharmaceutical product from a second syringe into the at least one of the plurality of pharmaceutical containers through the corresponding pierceable pharmaceutical container closure via a second syringe needle.

10. The method of claim 9, wherein the providing an aseptically sealable chamber comprises providing an aseptically sealable chamber comprising a syringe store, and wherein the second syringe is prepared by:
    aseptically mounting to the transfer wall a second source pharmaceutical container aseptically pre-sealed with a corresponding pierceable second pharmaceutical container closure and containing the second fluid pharmaceutical, wherein the mounting of the second source pharmaceutical container comprises disposing the second source pharmaceutical container in a location and orientation wherein the second pharmaceutical container closure is penetrable from within the interior of the sealable chamber,
    operating the robotic arm to place the first syringe in the syringe store,
    operating the robotic arm to obtain from the syringe store the second pharmaceutical syringe comprising the second syringe needle,
    operating the robotic arm to pierce the closure of the second source pharmaceutical container with the second syringe needle, and
    operating the robotic arm to extract a portion of the second fluid pharmaceutical product from the second source pharmaceutical container into the syringe.

11. The method of claim 1, wherein the establishing an aseptic condition comprises treating the interior of the sealable chamber and all portions of the at least one pharmaceutical container exposed to the interior of the sealable chamber with at least one of heated water vapor, gaseous hydrogen peroxide, ozone, nitrogen dioxide, ethylene oxide, and glutaraldehyde vapor.

12. The method of claim 1 wherein the sealing structure further includes a cap connected to the flange.

13. The method of claim 12 wherein the at least one container is disposed within the flange and cap.

14. The method of claim 13 wherein a pierceable closure is aseptically sealed with the at least one container.

15. The method of claim 14 wherein the at least one container is aseptically sealed to the sealing structure by at least one o-ring.

16. The method of claim 1 wherein the step of providing within the sealable chamber a first pharmaceutical syringe comprising a first syringe needle includes removing a cap from the first syringe at a syringe capping station.

17. The method of claim 1 wherein the step of aseptically mounting to the transfer wall a plurality of containers aseptically pre-sealed with corresponding pierceable pharmaceutical container closures, involves mounting to a side of the transfer wall with is exterior of the sealable chamber prior to the step of providing an aseptically sealable chamber.

18. A method for filling pharmaceutical containers with a fluid pharmaceutical product, the method comprising:
    providing an aseptically sealable chamber comprising a robotic arm and a transfer wall capable of having aseptically mounted thereto a plurality of pharmaceutical containers pre-sealed with pierceable closures, wherein the aseptically sealable chamber is capable of maintaining an aseptic condition within an interior of the sealable chamber when the pharmaceutical containers are mounted to the transfer wall,
    aseptically mounting to the transfer wall a plurality of pharmaceutical containers aseptically pre-sealed with corresponding pierceable pharmaceutical container closures, wherein the mounting of the plurality of pharmaceutical containers comprises mounting the plurality of pharmaceutical containers in locations and orientations wherein the corresponding pierceable pharmaceutical container closures are penetrable from within the interior of the sealable chamber, wherein the step of aseptically mounting to the transfer wall a plurality of pharmaceutical containers includes using at least one sealing structure to mount at least one intravenous bag to the transfer wall, the intra-venous bag includes a tube aseptically sealed to a pierceable closure, and the sealing structure includes two half-annular caps holding the pierceable closure of the intra-venous bag;
    providing within the sealable chamber a first pharmaceutical syringe comprising a first syringe needle,
    aseptically sealing the sealable chamber,
    establishing an aseptic condition within the interior of the sealable chamber and on all portions of the plurality of pharmaceutical containers exposed to the interior of the sealable chamber, and
    transferring a portion of the first fluid pharmaceutical product between the first syringe and at least one of the plurality of pharmaceutical containers through the corresponding pierceable pharmaceutical container closure via the first syringe needle.

19. The method of claim 18 wherein at least two sealing structures are disposed on a mounting plate and aseptically sealed to the transfer wall.

20. The method of claim 18, wherein the transferring comprises piercing the corresponding pierceable pharmaceutical container closure with the first syringe needle.

21. The method of claim 18, wherein the transferring comprises operating the robotic arm.

22. The method of claim 18, wherein providing an aseptically sealable chamber comprising a robotic arm comprises providing an aseptically sealable chamber comprising an articulated robotic arm and the transferring comprises operating the articulated robotic arm.

23. The method of claim 18, wherein the transferring includes injecting a portion of the first pharmaceutical product into the one of the plurality of pharmaceutical containers, and wherein providing within the sealable chamber the first pharmaceutical syringe containing the first fluid pharmaceutical product comprises:
    aseptically mounting to the transfer wall a first source pharmaceutical container aseptically pre-sealed with a corresponding pierceable first pharmaceutical container closure, wherein the mounting of the first source pharmaceutical container comprises disposing the first source pharmaceutical container in a location and orientation wherein the first pharmaceutical container closure is penetrable from within the interior of the sealable chamber,
    piercing the closure of the first source pharmaceutical container with the first syringe needle, and
    extracting a portion of the first fluid pharmaceutical product from the first source pharmaceutical container into the first pharmaceutical syringe.

24. The method of claim 23, wherein at least one of the aseptically sealing, the establishing an aseptic condition, the transferring, and the extracting a portion of the first fluid pharmaceutical product is performed automatically.

25. The method of claim 23, further comprising establishing within the sealable chamber a positive atmospheric pressure.

26. The method of claim 25, wherein the establishing within the sealable chamber a positive atmospheric pressure is performed automatically after the aseptically sealing the sealable chamber.

27. The method of claim 23, further comprising
    injecting a portion of a second fluid pharmaceutical product from a second syringe into the at least one of the plurality of pharmaceutical containers through the corresponding pierceable pharmaceutical container closure via a second syringe needle.

28. The method of claim 27, wherein the providing an aseptically sealable chamber comprises providing an aseptically sealable chamber comprising a syringe store, and wherein the second syringe is prepared by:
    aseptically mounting to the transfer wall a second source pharmaceutical container aseptically pre-sealed with a corresponding pierceable second pharmaceutical container closure and containing the second fluid pharmaceutical, wherein the mounting of the second source pharmaceutical container comprises disposing the second source pharmaceutical container in a location and orientation wherein the second pharmaceutical container closure is penetrable from within the interior of the sealable chamber,
    operating the robotic arm to place the first syringe in the syringe store,
    operating the robotic arm to obtain from the syringe store the second pharmaceutical syringe comprising the second syringe needle,
    operating the robotic arm to pierce the closure of the second source pharmaceutical container with the second syringe needle, and
    operating the robotic arm to extract a portion of the second fluid pharmaceutical product from the second source pharmaceutical container into the syringe.

29. The method of claim 18, wherein the establishing an aseptic condition comprises treating the interior of the sealable chamber and all portions of the at least one pharmaceutical container exposed to the interior of the sealable chamber with at least one of heated water vapor, gaseous hydrogen peroxide, ozone, nitrogen dioxide, ethylene oxide, and glutaraldehyde vapor.

30. The method of claim 18 wherein the step of providing within the sealable chamber a first pharmaceutical syringe comprising a first syringe needle includes removing a cap from the first syringe at a syringe capping station.

31. The method of claim 18 wherein the step of aseptically mounting to the transfer wall a plurality of containers aseptically pre-sealed with corresponding pierceable pharmaceutical container closures, involves mounting to a side of the transfer wall with is exterior of the sealable chamber prior to the step of providing an aseptically sealable chamber.

* * * * *